United States Patent [19]

Oosaka

[11] Patent Number: 4,733,084
[45] Date of Patent: Mar. 22, 1988

[54] METHOD OF DETECTION AND QUANTITATIVE DETERMINATION OF SULFUR AND SULFUR MONITOR USING THE METHOD

[75] Inventor: Hajime Oosaka, Osaka, Japan

[73] Assignee: Sumitomo Electric Industries, Ltd., Osaka, Japan

[21] Appl. No.: 816,843

[22] Filed: Jan. 7, 1986

[30] Foreign Application Priority Data

| Jan. 9, 1985 | [JP] | Japan | 60-943 |
| Jan. 9, 1985 | [JP] | Japan | 60-944 |
| Jan. 9, 1985 | [JP] | Japan | 60-945 |

[51] Int. Cl.$^4$ ............................................. G01N 21/33
[52] U.S. Cl. .................................................... 250/373
[58] Field of Search ................. 356/51, 320; 250/343, 250/373

[56] References Cited

U.S. PATENT DOCUMENTS

| 3,969,626 | 7/1976 | Saltzman | 250/343 |
| 4,563,585 | 1/1986 | Ward | 250/373 |

OTHER PUBLICATIONS

Optical Properties of Selenium by Heikki M. Isomaki, Physical Review B, vol. 26, No. 8, pp. 4485–4494, (Mar. 22, 1982).

Optical Loss in Selenium Thin Films as a Measure of Crystallinity by K. Harnisch, S. M. Neubacher, and O. Ennemoser, Short Notes K87–91, (Sep. 17, 1981).

Primary Examiner—F. L. Evans
Attorney, Agent, or Firm—Cushman, Darby & Cushman

[57] ABSTRACT

A method and apparatus for making a quantitative determination of gaseous sulfur. The sulfur is illuminated with light having one or more spectral lines selected from a first group of peaks including positive peaks at wavelengths in nm of 263, 265.5, 268, 270.5, 273, 276, 279 and 282, and from a second group of peaks including negative peaks at wavelengths in nm of 264.5, 267, 269.5, 272, 275, 278 and 281. The absorption by the sulfur of the illuminating light is measured and this absorption is analyzed to determined sulfur content.

4 Claims, 6 Drawing Figures

METHOD OF DETECTION AND QUANTITATIVE DETERMINATION OF SULFUR AND SULFUR MONITOR USING THE METHOD

BACKGROUND OF THE INVENTION

1. Field of Invention

The present invention relates to an arrangement (including both method and apparatus) for quantifying sulfur. The arrangement is capable of sensitive detection and quantitative determination of sulfur on site.

The apparatus of the present invention is useful as a high-sensitivity monitor for detection and quantitative determination of the sulfur that is present in semiconductor devices or which has resulted from their fabrication or waste disposal equipment, such as epitaxial growth apparatus (e.g. CVD and LPE furnaces) for compound semiconductors like ZnS, CdS and $ZnS_xSe_{1-x}$, high-pressure HB (horizontal Bridgman) furnace, annealing furnace, sulfur pressure annealing furnace, MBE apparatus and organometallic vapor phase epitaxy growth apparatus. The present invention is also suitable for use with melting furnaces for sulfur-containing alloys, ceramics and glass.

2. Prior Art

Few methods are known that are non-destructive, inert to the system and which are capable of on-the-spot detection and quantitative determination of gaseous sulfur. Most of the methods known today for sulfur detection are destructive. Gas chromatography is one of the non-destructive methods for detection and quantitative determination of gaseous substances. However, it is not suitable for sulfur detection because of the following inherent disadvantages: (1) part of the sample in solution being introduced into the measuring system will stick to the inside surface of an injection port, thereby rendering accurate determination of the sample impossible, and (2) the sampling which is indispensable to gas chromatography will disturb the system.

Atomic absorption spectroscopy allows for precise determination of an atomic sample vapor but is theoretically impossible unless the sample is heated to the temperature of atomization (2,000° C.) or above. In addition, no hollow cathode lamp exists that is suitable for use as a source of radiation in atomic absorption spectroscopic analysis of sulfur.

SUMMARY OF THE INVENTION

One object, therefore, of the present invention is to provide a method for detection and quantitative determination of gaseous sulfur that is non-destructive, inert to the measuring system and which is capable of high-sensitivity detection on site.

Another object of the present invention is to provide a highly sensitive sulfur monitor utilizing this method.

In accordance with the method of the present invention, a sample of gaseous sulfur is illuminated by at least one spectral line selected from a first group of peaks comprising positive peaks at wavelengths in nm of 263, 265.5, 268, 270.5, 273, 276, 279 and 282, and from a second group of peaks comprising negative peaks at wavelengths in nm of 264.5, 267, 269.5, 272, 275, 278 and 281. The absorption of these incident spectral lines by the gaseous sulfur is analyzed; and detection and quantitative determination of sulfur is performed on the basis of the height of each peak for the intensity of light.

The sulfur monitor of the present invention employing this method includes a furnace or a vessel with a built-in heater. A pair of windows provided in the furnace or vessel in the direction such that light generated by a light source can pass through a first of these windows, then pass through the vessel, and finally emerge through a second of these windows. The light source emits light including at least one spectral line selected from a first group of peaks comprising positive peaks at wavelengths in nm of 263, 265.5, 268, 270.5, 273, 276, 279 and 282, and from a second group of peaks comprising negative peaks at wavelengths in nm of 264.5, 267, 269.5, 272, 275, 278 and 281. At the second window is positioned a light-receiving photometric unit for performing detection and quantitative determination of sulfur on the basis of the height of peak intensity of any one of the spectral lines transmitting through the gaseous sulfur sample in the furnace or vessel.

DETAILED DESCRIPTION OF THE INVENTION

As a result of various studies made on the absorption spectra of gaseous sulfur samples in the form of $S_2$, $S_4$, $S_6$, $S_8$, etc., the present inventors have found that the spectra contained a first group of positive absorption peaks at wavelengths in nm of 263, 265.5, 268, 270.5, 273, 276, 279 and 282, and a second group of negative absorption peaks at wavelengths in nm of 264.5, 267, 269.5, 272, 275, 278 and 281. The inventors have also found that these two groups of peaks are obtained in the spectrum of molecular sulfur produced at a temperature of about 300° C. By using the peak of at least one of the fifteen spectral lines indicated above that result from the absorption of gaseous sulfur, the present invention will allow for on site detection and quantitative determination of gaseous sulfur with high sensitivity.

Figure 1:
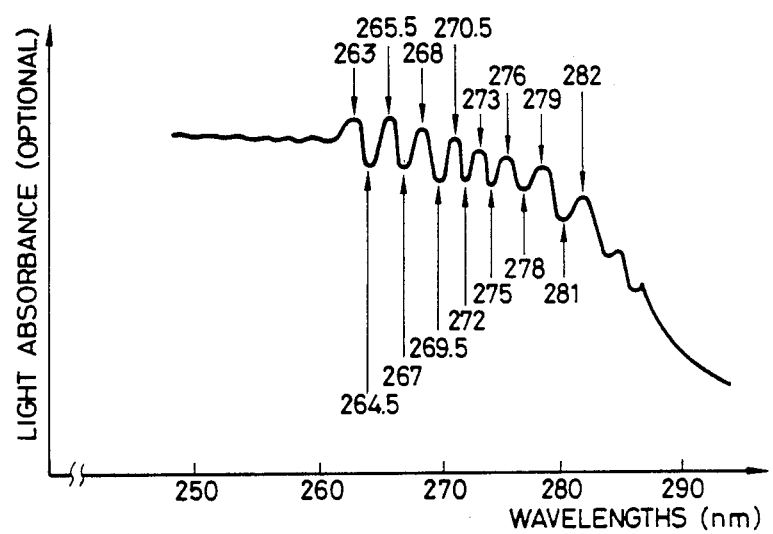
FIG. 1 is a graphical representation of the absorption spectrum of gaseous sulfur.
Figure 2:
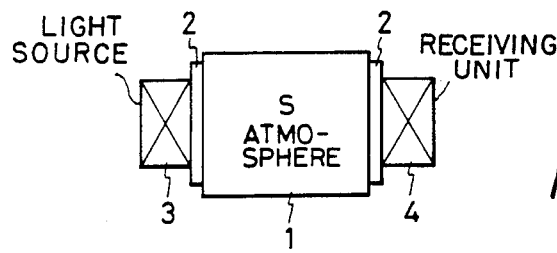
FIG. 2 is a schematic diagram of the present invention.

The concept of the present invention is shown diagrammatically in FIG. 2. The system comprises a furnace or a cell or tube 1 with a built-in heater, a pair of windows 2 provided at the ends of the furnace, cell or tube 1, and a light source 3 emitting wavelengths with spectral lines containing the two groups of peaks listed above. Light from light source 3 enters the furnace, cell or tube 1 through the left window 2 and emerges therefrom through the window 2 at the other end. The heights of the peak intensities of individual spectral lines of the emerging light are measured in a light-receiving unit 4, thereby detecting and quantitatively determining the sulfur in the furnace, cell or tube.

The theoretical basis for the detection and quantitative determination of sulfur is that the absorption for the peaks in the first and second groups is proportional to the concentration of sulfur, as expressed by the following equations:

$$D = \log(1/T(\%)) \tag{1}$$

$$D \propto C (D = kC) \tag{2}$$

where T is the precent absorbance at peak, C is the concentration of sulfur, D is a parameter associated with C, and k is a proportionality constant.

A hollow cathode lamp is used as the source for emitting spectral lines containing the peaks of the first and second groups and may be equipped with filters 7 through which only the spectral lines corresponding to the specific peaks will pass. Such filters 7 may be provided in the light-receiving unit 4.

The results of detection may be processed by a computer and displayed on CRT. Being capable of detecting and quantitatively determining sulfur on a semi-real time (substantially real time) basis, this technique will provide a sensitive sulfur monitor capable of on-the-spot detection and quantitative determination of sulfur and control of the sulfur input and pressure.

Figure 3A:
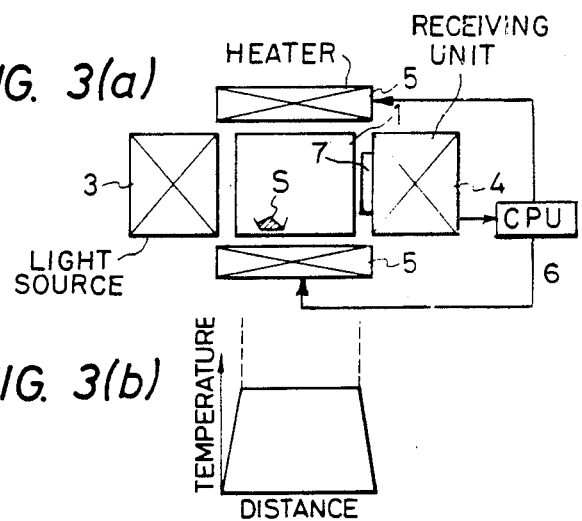
FIG. 3(a) is a schematic diagram of the apparatus employed in one embodiment of the present invention.
Figure 3B:
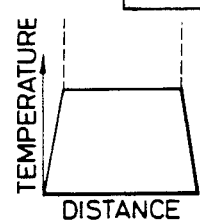
FIG. 3(b) is a graph showing the temperature distribution in the apparatus in FIG. 3(a)
Figure 4:
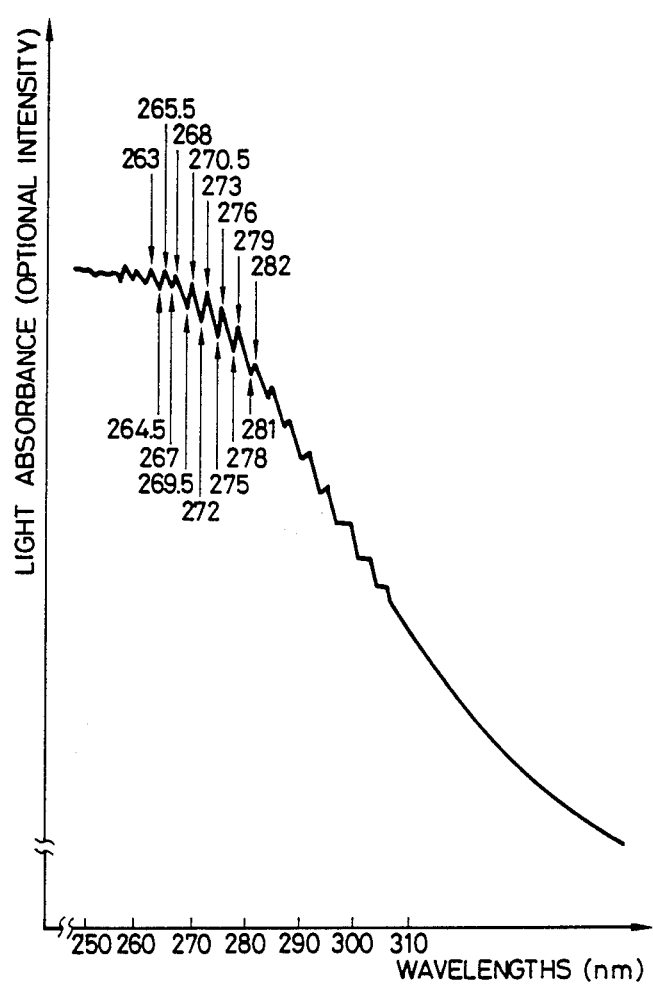
FIG. 4 is a graph plotting the wavelength vs. absorbance profile obtained in one embodiment of the present invention.

FIG. 3(a) is a schematic diagram of the apparatus used in one embodiment of the present invention which comprises a cell 1, a pair of windows 2, a light source 3, a light-receiving unit 4, filters 7 and heating elements 5. This apparatus provides a temperature distribution as shown in the graph of FIG. 3(b). The computer (CPU) 6 may be a personal computer. CPU 6 calculates in accordance with equations set forth in the present specification. FIG. 4 shows the absorption spectrum obtained by heating a gaseous sulfur sample S in the cell 1 at 298° C. The spectrum contained a first group of peaks (positive) at wavelengths in nm of 263, 265.5, 268, 270.5, 273, 276, 279 and 282, as well as a second group of peaks (negative) at wavelengths in nm of 264.5, 267, 269.5, 272, 275, 278 and 281.

Figure 5:
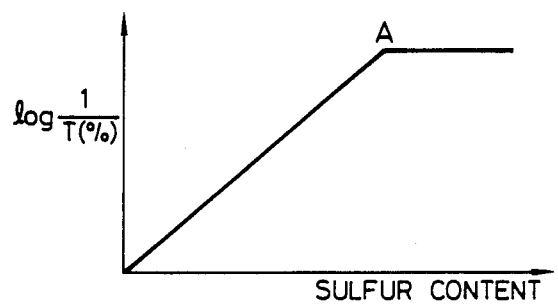
FIG. 5 is a graph showing the relationship between sulfur content and absorbance.

By careful experimentation, the inventors found that the profile depicted in FIG. 5 generally exists for the relationship between the sulfur input and light absorbance. If the intensity of light detected in the presence of a gaseous sulfur sample is denoted by I and the intensity of light detected in the absence of gaseous sulfur is indicated by Io, the present light absorbance is given by Equation (3):

$$T = (I/Io) \times 100 \tag{3}$$

It then follows that the quantity of sulfur can be determined from the absorbance by Equations (1) and (2). In FIG. 5, "A" represents the point of saturation at a temperature t, and is defined in terms of the vapor pressure of sulfur as follows:

$$\log P(t)(\text{mmHg}) = -(6750/t) + 11.32.$$

The relationship shown in FIG. 5 is valid for all of the absorption peaks in the first and second groups and, therefore, the amount of sulfur can be determined by measuring any one of the peaks obtained in the absorption spectrum. In accordance with the present invention, sulfur can be detected to a precision on the order of 0.01 ppm.

In accordance with another embodiment of the present invention, all or any number of the fifteen spectral lines for the peaks in the first and second groups may be detected, whereby the sulfur content can be determined from the heights of the individual peaks. In this case, Equation (1) and Equation (3) are replaced by the following mathematical expressions (a) to (c):

$$D = \log \frac{1}{\overline{T}(\%)}, \quad \overline{T}(\%) = \frac{1}{n} \sum_{i=1}^{i=n} \frac{I_i}{I_{oi}} \times 100 \tag{a}$$

$$\overline{D} = \frac{1}{n} \sum_{i=1}^{i=n} \log \frac{1}{Ti(\%)}, \quad Ti(\%) = \frac{I_i}{I_{oi}} \times 100 \tag{b}$$

$$D = \log \frac{1}{To(\%)}, \quad To(\%) = \frac{\sum_{i=1}^{i=n} I_i}{\sum_{i=1}^{i=n} I_{oi}} \times 100 \tag{c}$$

$$n = 1, 2, \ldots 15$$

where D and T are means of D and T, respectively and n (=1, 2, ... 15) represents the measurement for the corresponding number of peaks.

The evaluation of sulfur content by this approach can be easily and quickly realized with the aid of a computer and other calculating devices, and the measuring system can be controlled while displaying the observed sulfur content on a semi-real time basis.

The present invention has the following advantages:

By making use of the spectrum containing a first group of peaks (positive) and a second group of peaks (negative) that result from the absorption of gaseous sulfur, the invention realized on-the-spot and highly sensitive detection and quantitative determination of gaseous sulfur.

Since the heights of the spectral peaks for the first and second groups are used simultaneously, sulfur can be detected very precisely without any overlapping with other substances, and the precision of quantitative measurement of sulfur is improved significantly.

The high-sensitivity sulfur monitor of the present invention enables on-the-spot detection and quantitative determination of sulfur, and if the monitor is combined with a computer or other calculating devices, semi-real time detection and quantitative determination of sulfur can be performed on the basis of the absorbance for peaks in the spectrum, with the result that output signals from the calculator can be used as data for on-site control of the sulfur input and pressure.

Other embodiment and modification of the present invention will be apparent to those of ordinary skill in the art having the benefit of the teaching presented in the foregoing description and drawings. It is therefore, to be understood that this invention is not to be unduly limited and such modifications are intended to be included within the scope of the appended claims.

What is claimed is:

1. A method of detection and quantitative determination of gaseous sulfur comprising the steps of:
    illuminating a gaseous sulfur sample with light having at least one spectral line selected from a first group of peaks consisting of positive peaks at wavelengths in nm of 263, 265.5, 268, 270.5, 273, 276, 279 and 282, and from a second group of peaks consisting of negative peaks at wavelengths in nm of 264.5, 267, 269.5, 272, 275, 278 and 281;
    determining the amount of absorption of the illuminating light spectral lines by the sample; and
    performing detection and quantitative determination of the sulfur on the basis of the height of peak intensity of light of any one of the spectral lines transmitted through said gaseous sulfur sample.

2. A sulfur monitor comprising:

a vessel with a built-in heater filled with a gaseous sulfur sample;

a pair of windows provided in said vessel in the direction in which light travels;

a light source means for emitting into a first of said windows at least one spectral line selected from a first group of peaks consisting of positive peaks at wavelengths in nm of 263, 265.5, 268, 270.5, 273, 276, 279 and 282, and from a second group of peaks consisting of negative peaks at wavelengths in nm of 264.5, 267, 269.5, 272, 275, 278 and 281; and a light-receiving photometric unit positioned so as to receive light having passed through said gaseous sulfur sample for performing detection of the height of peak intensity of any one of the spectral lines transmitted through said gaseous sulfur sample in said vessel; and a computer means for quantitatively determining sulfur on the basis of said height, whereby the sulfur input and pressure are controlled on a semi-real time basis.

3. A sulfur monitor according to claim 2 wherein said light source means comprises a hollow cathode lamp.

4. A sulfur monitor according to claim 2 further comprising filters in a path of said light through which only the spectral lines having the peaks of the first and second groups may pass.

* * * * *